(12) United States Patent
Midorikawa et al.

(10) Patent No.: US 9,809,511 B2
(45) Date of Patent: Nov. 7, 2017

(54) METHOD FOR PRODUCING CONJUGATED DIOLEFIN

(71) Applicant: Asahi Kasei Chemicals Corporation, Tokyo (JP)

(72) Inventors: Hideo Midorikawa, Tokyo (JP); Mamoru Watanabe, Tokyo (JP)

(73) Assignee: ASAHI KASEI CHEMICALS CORPORATION, Tokyo (JP)

( * ) Notice: Subject to any disclaimer, the term of this patent is extended or adjusted under 35 U.S.C. 154(b) by 139 days.

(21) Appl. No.: 14/427,794

(22) PCT Filed: Oct. 16, 2013

(86) PCT No.: PCT/JP2013/078107
§ 371 (c)(1),
(2) Date: Mar. 12, 2015

(87) PCT Pub. No.: WO2014/061711
PCT Pub. Date: Apr. 24, 2014

(65) Prior Publication Data
US 2015/0210614 A1    Jul. 30, 2015

(30) Foreign Application Priority Data
Oct. 17, 2012  (JP) ................ 2012-230223

(51) Int. Cl.
| | | |
|---|---|---|
| C07C 5/48 | (2006.01) | |
| B01J 37/08 | (2006.01) | |
| B01J 23/887 | (2006.01) | |
| B01J 37/00 | (2006.01) | |

(52) U.S. Cl.
CPC ............ C07C 5/48 (2013.01); B01J 23/8872 (2013.01); B01J 37/0045 (2013.01); B01J 37/08 (2013.01);
(Continued)

(58) Field of Classification Search
CPC ................ C07C 5/48; C07C 2523/883; C07C 2523/887; C07C 2523/10;
(Continued)

(56) References Cited

U.S. PATENT DOCUMENTS

| | | |
|---|---|---|
| 2012/0130137 A1 | 5/2012 | Orita et al. |
| 2014/0114108 A1 | 4/2014 | Yano et al. |

FOREIGN PATENT DOCUMENTS

| | | |
|---|---|---|
| CN | 103534226 A | 1/2014 |
| JP | 2-19370 A | 1/1990 |

(Continued)

OTHER PUBLICATIONS

Rubio et al. ("Two-zone Fluidized Bed Reactor for Simultaneous Reaction and Catalyst Reoxidation: Influence of Reactor Size" Applied Catalysis A: General 272.1 (2004): 321-327).*

(Continued)

*Primary Examiner* — Brian McCaig
*Assistant Examiner* — Jason Chong
(74) *Attorney, Agent, or Firm* — Birch, Stewart, Kolasch & Birch, LLP

(57) ABSTRACT

A method for producing a conjugated diolefin is configured as follows. A monoolefin having four or more carbon atoms is fed from a plurality of monoolefin feed nozzles. In addition, at least 50% or more of a total amount of an oxygen-containing gas is fed from an oxygen-containing gas feed nozzle located at a bottom of a fluidized bed reactor. Furthermore, the plurality of monoolefin feed nozzles at n places located at heights a1, a2, . . . , and an from the oxygen-containing gas feed nozzle, respectively, feed the monoolefin having four or more carbon atoms at ratios of b1, b2, . . . , bn (b1+b2+ . . . +bn=1), respectively. Furthermore, a weighted mean value represented by the following formula is 100 mm or greater:

weighted mean value=$a1*b1+a2*b2+ \ldots +an*bn$.

13 Claims, 5 Drawing Sheets

(52) U.S. Cl.
CPC ....... *B01J 2523/00* (2013.01); *C07C 2521/08* (2013.01); *C07C 2523/02* (2013.01); *C07C 2523/04* (2013.01); *C07C 2523/10* (2013.01); *C07C 2523/18* (2013.01); *C07C 2523/28* (2013.01); *C07C 2523/745* (2013.01); *C07C 2523/755* (2013.01); *C07C 2523/883* (2013.01); *C07C 2523/887* (2013.01)

(58) Field of Classification Search
CPC .......... C07C 2523/755; C07C 2523/18; C07C 2523/04; C07C 2523/28; B01J 37/0045; B01J 23/8872; B01J 37/08; B01J 2523/00; Y02P 20/52
See application file for complete search history.

(56) References Cited

FOREIGN PATENT DOCUMENTS

| | | |
|---|---|---|
| JP | 8-27087 A | 1/1996 |
| JP | 2010-120933 A | 6/2010 |
| JP | 2012-67047 A | 4/2012 |
| JP | 2012-72076 A | 4/2012 |
| JP | 2012-92092 A | 5/2012 |
| TW | 201228731 A | 7/2012 |
| WO | WO 2010/137595 A1 | 12/2010 |

OTHER PUBLICATIONS

International Prelminary Report on Patentability and Written Opinion dated Apr. 30, 2015, in PCT International Application No. PCT/JP2013/078107, with English translation.

International Search Report dated Jan. 21, 2014, in PCT International Application No. PCT/JP2013/078107, with English translation.

Ishigaki, S., "Novel Fluidized Bed Reactor," Chemical Engineering (Aug. 1999), pp. 44-48, with English translation.

Supplementary European Search Report dated Dec. 4, 2015, in European Patent Application No. 13847086.9.

* cited by examiner

[FIG. 1]
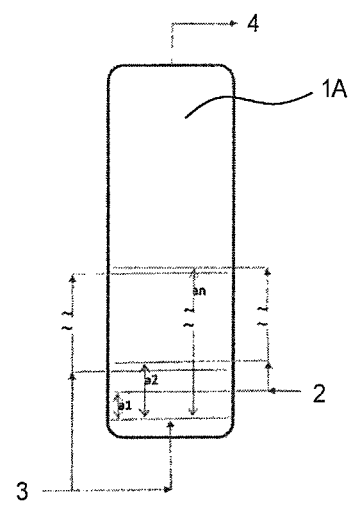

[FIG. 2]
(a)
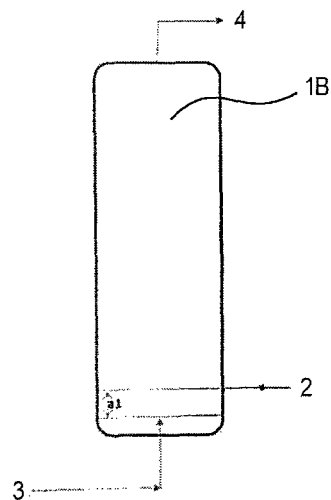
(b)
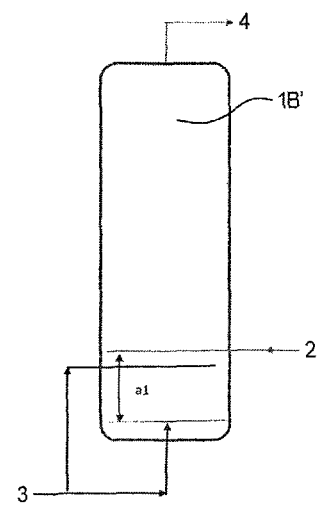

[FIG. 3]
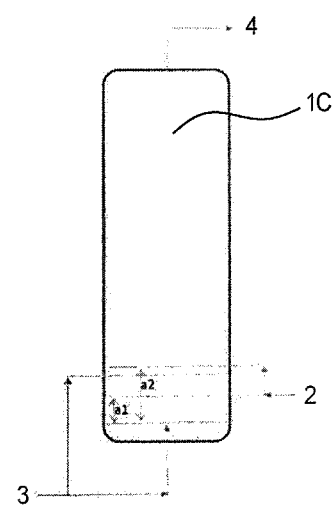

[FIG. 4]
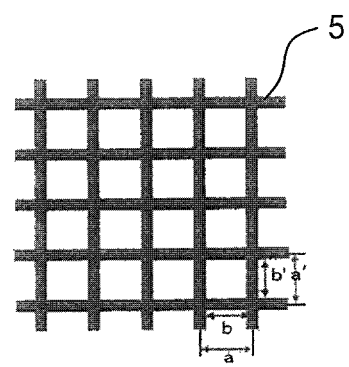

[FIG. 5]
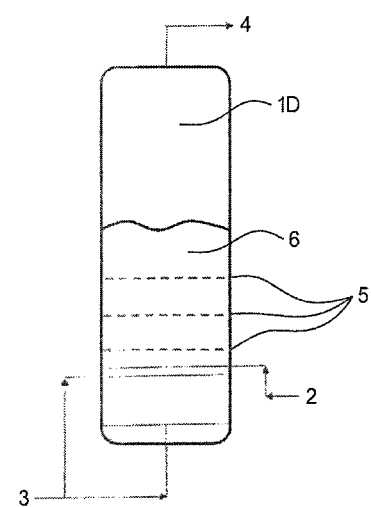

METHOD FOR PRODUCING CONJUGATED DIOLEFIN

TECHNICAL FIELD

The present invention relates to a method for producing a conjugated diolefin by a fluidized bed reaction method using an oxide catalyst.

BACKGROUND ART

A method for producing conjugated diolefins, for example, 1,3-butadiene and isoprene, corresponding to monoolefins having four or more carbon atoms, such as n-butene and isopentene, by the catalytic oxidative dehydrogenation reactions of these monoolefins in contact with molecular oxygen is well known. A large number of catalysts used in the above oxidative dehydrogenation reactions are proposed.

The important reactions in the chemical industry are heterogeneous reactions involving two phases, such as gas-solid. For example, ammonia synthesis, ethylene oxide synthesis, and the catalytic cracking of petroleum are known as heterogeneous reactions industrially using oxide catalysts.

Reaction methods in which oxide catalysts are used include a fixed bed, a fluidized bed, and a moving bed. Among these, the fixed bed reaction method is often industrially used, making the most of the advantage of being able to increase reaction yield since the gas flow state is similar to an extrusion flow. However, the fixed bed reaction method has low heat transfer properties, and can be said to be unsuitable for exothermic reactions and endothermic reactions, which require heat removal and heating. Particularly, when the fixed bed reaction method is applied to an intense exothermic reaction, such as an oxidation reaction, the temperature increases suddenly to make control difficult, and the reaction may get out of control. A further problem is that the catalyst is damaged by such a sudden temperature increase, and deteriorates early. For example, an oxidative dehydrogenation reaction in which 1,3-butadiene is synthesized from butene is an exothermic reaction with about 30 kcal/mol.

The fluidized bed reaction method is characterized in that catalyst particles flow intensely in a reactor. Because of such a characteristic, an advantage is that (1) during a reaction when the heat transfer properties are high and the reaction involving large heat generation or heat absorption, the temperature in the reactor can be kept substantially uniform, and excessive progress of the reaction can be suppressed. A further advantage is that (2) local accumulation of energy is suppressed, and thus, a raw material gas within the explosion range can be reacted, and the raw material concentration can be increased to improve productivity. Therefore, the fluidized bed reaction method is a reaction method suitable for the oxidative dehydrogenation reactions of hydrocarbons involving intense heat generation.

Patent Literature 1 describes applying the fluidized bed reaction method to the production of a conjugated diolefin. In addition, Patent Literature 2 describes a method for producing butadiene with the amount of carbon contained in a catalyst controlled in a specific range.

In addition, when conjugated diolefins, for example, 1,3-butadiene and isoprene, corresponding to monoolefins having four or more carbon atoms are produced by the catalytic oxidative dehydrogenation reactions of these monoolefins and molecular oxygen, organic matter adheres to the catalyst by the progress of the operation, and the amount of carbon on the catalyst increases. If this amount of carbon increases too much, the crushing of the catalyst, the deterioration of flowability, a decrease in the selectivity of the conjugated diolefins, and the like are caused, and it is difficult to stably produce the conjugated diolefins from the corresponding monoolefins. Therefore, it is necessary to provide a catalyst regeneration step in order to remove carbon adhering to the catalyst. Patent Literature 3 describes a method for regenerating a catalyst that has been used in such production of butadiene.

CITATION LIST

Patent Literature

Patent Literature 1: Japanese Patent Laid-Open No. 2010-120933

Patent Literature 2: Japanese Patent Laid-Open No. 2012-67047

Patent Literature 3: Japanese Patent Laid-Open No. 2012-92092

SUMMARY OF INVENTION

Technical Problem

However, when a catalyst is regenerated by the method described in Patent Literature 3, catalyst regeneration equipment is required. Further, the step of extracting and conveying the catalyst, and the step of treating the catalyst to which carbon adheres, at high temperature are essential, and therefore, the operation is complicated. In addition, an oxide catalyst containing molybdenum has a relatively low melting point. Therefore, a problem is that in the step of treating the catalyst to which carbon adheres, at high temperature, sintering due to heat occurs, and the activity is likely to decrease.

The present invention has been made in view of the above problems. Specifically, it is an object of the present invention to provide a method for stably producing, from a monoolefin having four or more carbon atoms, the corresponding conjugated diolefin with high yield while carbon adhering to a catalyst can be suppressed without installing catalyst regeneration equipment.

Solution to Problem

The present inventor has studied diligently in order to solve the above problems, and, as a result, found that a conjugated diolefin can be stably produced without installing catalyst regeneration equipment, by setting, to a specific value or more, a weighted mean value considering the positions of nozzles for feeding a monoolefin having four or more carbon atoms and feed proportion, leading to the completion of the present invention.

Specifically, the present invention is as follows.

[1] A method for producing a conjugated diolefin, comprising a step of feeding a monoolefin having four or more carbon atoms and an oxygen-containing gas into a fluidized bed reactor having an oxide catalyst containing molybdenum thereinside, and bringing the oxide catalyst, the monoolefin having four or more carbon atoms, and the oxygen-containing gas into contact with each other to produce a conjugated diolefin, wherein the monoolefin having four or more carbon atoms is fed from a monoolefin feed nozzle(s) installed at n place(s) (n=1, 2, . . . , n), at least 50% or more of a total amount of the oxygen-containing gas is fed from an oxygen-containing gas feed nozzle located at a bottom of the fluidized bed reactor, the monoolefin feed nozzles at distances a1, a2, . . . , an from the oxygen-containing gas feed nozzle feed the monoolefin having four or more carbon atoms at ratios of b1, b2, . . . , bn (b1+b2+ . . . +bn=1), respectively, and a weighted mean value represented by a following formula and obtained from the distances and the ratios is 100 mm or more.

weighted mean value=a1*b1+a2*b2+ . . . +an*bn

[2] The method for producing a conjugated diolefin according to [1], wherein a number of the monoolefin feed nozzles per unit area is 10/m² or more.

[3] The method for producing a conjugated diolefin according to [1] or [2], wherein a network structure having an opening ratio of 60% or more is disposed above a position of the monoolefin feed nozzle.

[4] The method for producing a conjugated diolefin according to any one of [1] to [3], wherein feed of the monoolefin having four or more carbon atoms is performed at one stage.

[5] The method for producing a conjugated diolefin according to any one of [1] to [4], wherein the weighted mean value is 100 mm or more and 3000 mm or less.

[6] The method for producing a conjugated diolefin according to any one of [1] to [5], wherein the monoolefin having four or more carbon atoms is n-butene or isopentene.

[7] The method for producing a conjugated diolefin according to any one of [1] to [6], wherein the oxide is represented by the following empirical formula, and the support is one or more selected from the group consisting of silica, alumina, titania, and zirconia, $$Mo_{12}Bi_pFe_qA_aB_bC_cD_dE_eO_x$$

(wherein A is at least one element selected from nickel and cobalt, B is at least one element selected from alkali metal elements, C is at least one element selected from magnesium, calcium, strontium, barium, zinc, and manganese, D is at least one rare earth element, E is at least one element selected from chromium, indium, and gallium, O is oxygen, p, q, a, b, c, d, e, and x represent atomic ratios of bismuth, iron, A, B, C, D, E, and oxygen to 12 molybdenum atoms, respectively, $0.1 \le p \le 5$, $0.5 \le q \le 8$, $0 \le a \le 10$, $0.02 \le b \le 2$, $0 \le c \le 5$, $0 \le d \le 5$, and $0 \le e \le 5$ are satisfied, and x is a number of atoms of oxygen required to satisfy valence requirements of other elements present.)

[8] The method for producing a conjugated diolefin according to any one of [1] to [7], wherein the monoolefin having four or more carbon atoms, and at least one gas selected from the group consisting of nitrogen, water vapor, and carbon dioxide are fed from the monoolefin feed nozzle.

Advantageous Effects of Invention

According to the present invention, carbon adhering to a catalyst can be suppressed, and from a monoolefin having four or more carbon atoms, the corresponding conjugated diolefin can be stably produced with high yield.

BRIEF DESCRIPTION OF DRAWINGS

FIG. 1 is a schematic diagram when a monoolefin having four or more carbon atoms is fed at n stages;

FIG. 2(a) is a schematic diagram when a monoolefin having four or more carbon atoms is fed at one stage;

FIG. 2(b) is a schematic diagram when a monoolefin having four or more carbon atoms 2 is fed at one stage, and some of an oxygen-containing gas is fed so as to be opposed to the feed of the monoolefin having four or more carbon atoms 2;

FIG. 3 is a schematic diagram when a monoolefin having four or more carbon atoms is fed at two stages;

FIG. 4 is a schematic diagram of a network structure; and

FIG. 5 is a schematic diagram of a reactor in which network structures are disposed.

DESCRIPTION OF EMBODIMENTS

A mode for carrying out the present invention (hereinafter "this embodiment") will be described in detail below. It should be noted that the present invention is not limited to the following embodiment, and various modifications can be made with the scope of the present invention.

A method for producing a conjugated diolefin in this embodiment comprises the step of feeding a monoolefin having four or more carbon atoms 2 and an oxygen-containing gas 3 into a fluidized bed reactor in which an oxide catalyst containing molybdenum 6 is present, and bringing the oxide catalyst, the monoolefin having four or more carbon atoms 2, and the oxygen-containing gas 3 into contact with each other to produce a conjugated diolefin. Further, in the method for producing a conjugated diolefin in this embodiment, the above monoolefin having four or more carbon atoms 2 is fed from monoolefin feed nozzles installed at n place(s) (n=1, 2, . . . , n), and at least 50% or more of the total amount of the above oxygen-containing gas 3 is fed from oxygen-containing gas feed nozzles located at the bottom of the above fluidized bed reactor. It should be noted that, in the method for producing a conjugated diolefin in this embodiment, the monoolefin feed nozzles at distances a1, a2 . . . an from the above oxygen-containing gas feed nozzles feed the above monoolefin having four or more carbon atoms 2 at the ratios of b1, b2 . . . bn (b1+b2+ . . . +bn=1). Furthermore, in the method for producing a conjugated diolefin in this embodiment, a weighted mean value represented by the following formula and obtained from the above distances and the above ratios is 100 mm or more.

weighted mean value=a1*b1+a2*b2+ . . . +an*bn

Because of the configuration as described above, according to the method for producing a conjugated diolefin in this embodiment, carbon adhering to the catalyst can be suppressed, and from the monoolefin having four or more carbon atoms 2, the corresponding conjugated diolefin can be stably produced with high yield.

FIGS. 1, 2(a), and 3 respectively show schematic diagrams when the monoolefin having four or more carbon atoms 2 is fed to fluidized bed reactors 1A to 1C at n stages, one stage, and two stages to obtain a reaction-produced gas comprising a conjugated diolefin 4. The "fluidized bed reactor" may be simply described as the "reactor" below. In addition, FIG. 2(b) shows a schematic diagram when in a reactor 1B', the monoolefin having four or more carbon atoms 2 is fed at one stage, and some of the oxygen-containing gas is fed so as to be opposed to the feed of the monoolefin having four or more carbon atoms 2 to obtain the reaction-produced gas 4. In the aspects of FIGS. 1 and 3, the oxygen-containing gas 3 is fed not only from the reactor bottom but also from a higher position in the reactor. In addition, FIG. 4 shows a network structure 5, and FIG. 5 shows a schematic diagram in which the network structures 5 are installed in a fluidized bed reactor 1D. It should be noted that, in FIGS. 1 to 3, the illustration of the oxide catalyst containing molybdenum 6 is omitted, but in FIG. 5, the oxide catalyst containing molybdenum 6 is shown for confirmation.

[1] Method for Producing Conjugated Diolefin (1) Raw Material

In the production method in this embodiment, the monoolefin having four or more carbon atoms 2 is used as a raw material. A monoolefin has only one carbon-carbon double bond. Usually, a monoolefin is an organic compound having no functional group, and is a straight chain and/or a branched chain hydrocarbon. The upper limit of the number of carbon atoms is not particularly limited, but is preferably 6 or less from the viewpoint of reactivity. Examples of the monoolefin having four or more carbon atoms 2 include n-butene (1-butene and 2-butene), 1-pentene, 2-pentene, isopentene (2-methyl-1-butene and 3-methyl-1-butene), 1-hexene, 2-hexene, and 2,3-dimethylbutene. Among the above, n-butene or isopentene is preferably used as the monoolefin having four or more carbon atoms from the viewpoint of the versatility of the product. One monoolefin may be used as the raw material, or two or more monoolefins may be used as the raw material. It should be noted that a monoolefin that is liquid at an ordinary temperature of about 5° C. to 35° C. is preferably subjected to the reaction after being gasified using steam or a gasification apparatus having a heating portion, such as a heat transfer coil.

The monoolefin having four or more carbon atoms 2 need not always have high purity, and any mixture or an industrial grade may be used. For example, in the case of n-butene, n-butene produced by the dimerization of ethylene, a residual component (raffinate-1) obtained by extracting 1,3-butadiene from a C4 fraction produced as a by-product in naphtha pyrolysis, a residual component (raffinate-2) obtained by further extracting isobutylene, a butene fraction obtained by the dehydrogenation reaction or oxidative dehydrogenation reaction of n-butane, or a C4 fraction produced as a by-product in the catalytic conversion reaction of ethylene obtained by ethane pyrolysis or the dehydration reaction of biomass ethanol may be used. Biomass ethanol is ethanol obtained from plant resources, and specific examples thereof include ethanol obtained by the fermentation of sugarcane, corn, and the like, and ethanol obtained from woody resources, such as scrap wood, timber from forest thinning, rice straws, and crops.

The monoolefin having four or more carbon atoms 2 may comprise a paraffin, water, hydrogen, nitrogen, carbon dioxide, carbon monoxide, and the like. Examples of the paraffin can include methane, ethane, propane, butane, pentane, hexane, heptane, octane, and nonane. In addition, the monoolefin having four or more carbon atoms 2 may also contain oxygen outside the explosion range. In addition, after 1,3-butadiene, isoprene, or the like that is the target product is separated from the reaction product, at least some of unreacted butene, isopentene, or the like may also be recycled to the fluidized bed reactor.

The concentration of the monoolefin having four or more carbon atoms 2 fed to the reactor is preferably at least 2% by volume or more based on the amounts of all feed gases from the viewpoint of the productivity of the conjugated diolefin, and is preferably 30% by volume or less from the viewpoint of reducing the load on the catalyst. The concentration of the monoolefin having four or more carbon atoms 2 is more preferably 3% by volume or more and 25% by volume or less, further preferably 4% by volume or more and 20% by volume or less.

(2) Reactor

As the above fluidized bed reactor, one having a gas disperser, an internal, and a cyclone in the reactor as its main components, and having a structure that allows the catalyst to flow and brings the olefin that is the raw material and the oxygen-containing gas 3 into contact with the catalyst may be used. For example, usual fluidized bed reactors described in Ryudosho Handobukk (Fluidized Bed Handbook) (published by BAIFUKAN CO., LTD, 1999) and the like can be used, and particularly, bubbling fluidized bed type reactors are suitable. It should be noted that the "bottom" of the reactor refers to a bottom plate on which the nozzles that feed the oxygen-containing gas are located, but refers to the bottom plate of the reactor when the oxygen-containing gas is fed downward herein.

The monoolefin feed nozzle in this embodiment is a nozzle that feeds the monoolefin having four or more carbon atoms 2, and the oxygen-containing gas feed nozzle means a nozzle that feeds the gas containing oxygen. In the method for producing a conjugated diolefin in this embodiment, the oxygen-containing gas 3 and the monoolefin having four or more carbon atoms 2 can be fed in a single-stage or multistage manner.

In the method for producing a conjugated diolefin in this embodiment, when the monoolefin having four or more carbon atoms 2 is fed at n stage(s) (n=1, 2, . . . , n), the monoolefin having four or more carbon atoms 2 is fed at the ratios of b1, b2 . . . bn (b1+b2+ . . . +bn=1), respectively, from the monoolefin feed nozzles at the distances a1, a2 . . . an (a1<a2< . . . <an) from the oxygen-containing gas feed nozzles located at the bottom of the reactor. Here, by adjusting the weighted mean value represented by the following formula and obtained from the above distances and the above ratios to 100 mm or more, the adhesion of carbon to the oxide catalyst during the operation of the reactor can be suppressed.

$$\text{weighted mean value} = a1*b1 + a2*b2 + \ldots + an*bn$$

When the weighted mean value is 100 mm or more, a region having high oxygen concentration is locally formed in the reactor, and carbon adhering to the catalyst can be oxidized and removed. Here, the distance between the oxygen-containing gas feed nozzles located at the bottom of the reactor and the monoolefin feed nozzles indicates the distance between the gas blowoff tips of the respective nozzles.

It should be noted that the number n of the stages of the feed of the monoolefin having four or more carbon atoms 2 is not particularly limited. From the viewpoint of simplifying the equipment structure and further increasing the conversion rate of the fed monoolefin, n is preferably 3 or less, more preferably 2 or less, and particularly preferably 1. In addition, the values of the feed ratios b1, b2, . . . , bn at the stages are also not particularly limited, but are preferably b1≥b2≥ . . . ≥bn for a reason similar to the above.

From the viewpoint of more effectively removing carbon adhering to the catalyst, the above weighted mean value is preferably 100 mm or more and 3000 mm or less, more preferably 200 mm or more and 2000 mm or less, and further preferably 300 mm or more and 1500 mm or less.

As a particularly preferred embodiment, the feed of the monoolefin having four or more carbon atoms 2 is performed at one stage, and the distance between the monoolefin feed nozzles and the oxygen-containing gas feed nozzles is adjusted to 100 mm or more, preferably 200 mm or more and 2000 mm or less, and further preferably 300 mm or more and 1500 mm or less.

In addition, it is preferred that the monoolefin having four or more carbon atoms in this embodiment, and at least one gas selected from the group consisting of nitrogen, water vapor, and carbon dioxide are fed from the above monoolefin feed nozzles. When at least one inert gas selected from the group consisting of nitrogen, water vapor, and carbon dioxide is fed with the monoolefin having four or more carbon atoms 2, there is a tendency that the adhesion of carbon to the catalyst and the reduction of the catalyst are more effectively suppressed. This inert gas may be contained in an amount 0 to 5 times, preferably 0.5 to 3 times, further preferably 1 to 2 times, more than that of the monoolefin. In addition, a slight amount of oxygen may also be contained outside the explosion range of the monoolefin having four or more carbon atoms 2.

The oxygen-containing gas feed nozzles at the first stage in this embodiment may be installed upward from the bottom of the fluidized bed reactor or downward toward the bottom. When the oxygen-containing gas feed nozzles are installed downward, a state in which the gas is blown toward the reactor bottom is provided. The distance between these nozzle tips and the reactor bottom is not particularly limited, and is 100 mm or more and 1000 mm or less, preferably 200 mm or more and 800 mm or less, and further preferably 300 mm or more and 600 mm or less, from the viewpoints of fluidizing the catalyst at the reactor bottom, suppressing the crushing of the catalyst due to collision with the bottom plate, and preventing mechanical damage to the reactor bottom plate. In addition, also for the feed of the oxygen-containing gas 3 at the second and subsequent stages, the oxygen-containing gas feed nozzles may be appropriately installed upward or downward as described in the above.

In addition, from the viewpoint of further improving the contact between the monoolefin having four or more carbon atoms 2, oxygen, and the catalyst, it is preferred that a network structure 5 having an opening ratio of 60% or more is disposed above the feed position of the monoolefin having four or more carbon atoms 2. For the opening ratio of the network structure 5 in this embodiment, a value represented by $[(b/a) \times (b'/a')] \times 100(\%)$ as shown in FIG. 4 is used. The above a and a' each represent the distance between the centers of a steel material forming the network structure and a steel material adjacent to this steel material. In addition, the above b and b' each represent the distance between the inner sides of a steel material constituting the net and a steel material adjacent to this steel material. The opening ratio of the network structure 5 is 60% or more, preferably 70% or more and 99% or less, and further preferably 80% or more and 98% or less, from the viewpoint of ensuring the free passage of the fluidized bed catalyst well. In addition, the disposition interval of the network structure 5 with respect to the feed position of the monoolefin having four or more carbon atoms 2 may be 100 mm or more and 1000 mm or less, preferably 200 mm or more and 800 mm or less, further preferably 300 mm or more and 600 mm or less from the viewpoint of promoting the retention of the catalyst on the network structure 5. A schematic diagram of a reactor in which the network structures 5 are disposed is shown in FIG. 5.

The material of the network structure 5 is not particularly limited. For example, carbon steel and stainless may be used, and among them, SUS304 and SUS316 are preferred.

The number of the network structures 5 installed is not particularly limited, and is preferably 1 to 10, and further, more preferably 2 to 5.

In the production method in this embodiment, at least 50% or more of the total amount of the fed oxygen-containing gas is fed from the bottom of the reactor. Preferably 65% or more, more preferably 80% or more, of the total amount of the fed oxygen-containing gas is fed from the reactor bottom. In order to locally form a portion having high oxygen concentration in the reactor, it is necessary to feed a somewhat large amount of the oxygen-containing gas 3 from one place, and it is effective to feed the oxygen-containing gas 3 from the reactor bottom where a relatively large amount of the catalyst is present. The remaining oxygen-containing gas may be fed to a higher position where the catalyst inside the fluidized bed reactor is present. More preferably, the above remaining oxygen-containing gas is fed so as to be opposed to the monoolefin feed nozzles. In this case, the distance between the oxygen-containing gas feed nozzles located at the above-described upper portion and the monoolefin feed nozzles may be 50 mm or more and 500 mm or less. The above distance is preferably 75 mm or more and 300 mm or less, more preferably 100 mm or more and 200 mm or less. It should be noted that it is preferred that nitrogen, water, carbon monoxide, carbon dioxide, and the like are entrained in the fed oxygen-containing gas. In addition, the oxygen-containing gas may also comprise the monoolefin having four or more carbon atoms that is the raw material, a hydrocarbon compound, and the like in the range of the lower limit of explosion. In addition, some of the off-gas obtained by absorbing an organic component, such as butadiene, from the gas produced by the reaction, by an absorption step may also be fed.

As the source of oxygen, usually, air may be used, and in addition, a gas obtained by mixing oxygen and air, or the like to increase oxygen concentration, or a gas obtained by mixing air and an inert gas, such as helium or nitrogen, or the like to decrease oxygen concentration may also be used. From the viewpoint of making the contact between the monoolefin 2, oxygen, and the catalyst more efficient, the molar ratio of the monoolefin having four or more carbon atoms 2 to oxygen is preferably in the range of 1/0.4 to 2.5 (1.9 to 11.9), more preferably in the range of 1/0.6 to 2.1 (2.9 to 10), in terms of the monoolefin/oxygen (air).

In the production method in this embodiment, if the above-described weighted mean value is less than 100 mm, the oxidation reaction of the organic matter adhering to the catalyst is insufficient, and the amount of carbon on the catalyst increases by the progress of the operation. In addition, the upper limit of the weighted mean value is not particularly limited, but may be 3000 mm or less from the viewpoint of sufficiently ensuring the contact efficiency and contact time between the monoolefin having four or more carbon atoms 2, oxygen, and the catalyst. From a similar viewpoint, the above upper limit of the weighted mean value is preferably 2000 mm or less, more preferably 1500 mm or less.

In addition, the number of nozzles per unit area at each stage for the monoolefin feed nozzles and the oxygen-containing gas feed nozzles is not particularly limited, but is preferably $10/m^2$ or more, more preferably $13/m^2$ or more and $50/m^2$ or less, and further preferably $15/m^2$ or more and $30/m^2$ or less. The number of nozzles per unit area may be simply described as "nozzle density" herein. Thus, there is a tendency that the conversion rate of the monoolefin can be increased. The above conversion rate is preferably adjusted to 60% or more, more preferably 70% or more, and further preferably 80% or more.

In this embodiment, from the viewpoint of improving the contact between the fed monoolefin, oxygen, and the catalyst to increase the conversion rate, it is preferred that the monoolefin feed nozzles are opposed to the oxygen-containing gas feed nozzles on a 1:1 basis. However, as long as a predetermined weighted mean value in this embodiment described above is obtained, the number of monoolefin feed nozzles may be larger than the number of oxygen-containing gas feed nozzles, or on the contrary smaller. In addition, the nozzles need not always be opposed to each other. From the viewpoint of dispersing the monoolefin having four or more carbon atoms 2 as uniform as possible, it is preferred that the number of monoolefin feed nozzles is larger than the number of oxygen-containing gas feed nozzles. Also in the case of multiple stages, for a similar reason, it is preferred that the monoolefin feed nozzles are opposed to the oxygen-containing gas feed nozzles on a 1:1 basis, and from the viewpoint of uniformly dispersing the monoolefin, the number of monoolefin feed nozzles may be larger than the number of oxygen-containing gas feed nozzles. The monoolefin feed nozzles may be installed in either of upward and downward directions, but are preferably installed downward.

(3) Reaction Conditions

In the production method in this embodiment, the reaction temperature is preferably 300° C. or more and 450° C. or less, more preferably 320° C. or more and 420° C. or less, and further preferably 340° C. or more and 400° C. or less. When the above reaction temperature is 300° C. or more, there is a tendency that a sufficiently good conversion rate of the monoolefin can be ensured. When the above reaction temperature is 450° C. or less, there is a tendency that the combustion and decomposition of the produced conjugated diolefin can be effectively prevented. The conjugated diolefin production reaction is an exothermic reaction, and therefore, it is preferred that heat is removed to reach a preferred reaction temperature. The removal of the generated reaction heat may be performed, for example, using a cooling tube inserted into the reactor. The reaction temperature may be adjusted in the above range by the removal of reaction heat by the cooling tube, or the heat supply by a heating apparatus.

The reaction pressure in this embodiment may be in the range of slightly reduced pressure to 0.8 MPa. The contact time between the raw material mixed gas and the catalyst is in the following range. When the contact time is in the range of 1 to 20 (sec·g/cc), preferably 2 to 10 (sec·g/cc), with respect to the total amount of the fed gases, and the amount of the catalyst in the reactor, there is a tendency that the conjugated diolefin that is the target product can be preferably produced.

In this embodiment, the conjugated diolefin corresponding to the monoolefin is produced by the contact between the catalyst and the raw material mixed gas in the reactor. For example, when the monoolefin is n-butene, the main product is 1,3-butadiene. When the monoolefin is isopentene, the main product is isoprene. The yield and/or selectivity of the product depend on the raw material, the catalyst, the reaction temperature, and the like, and therefore may be appropriately set according to the target product.

In this embodiment, the gas comprising the produced conjugated diolefin (reaction-produced gas 4) flows out of the reactor outlet. The oxygen concentration in the reactor outlet gas is preferably 0% by volume or more and 3.0% by volume or less, more preferably 0.1% by volume or more and 2.5% by volume or less, and further preferably 0.2% by volume or more and 2.0% by volume or less. The oxygen concentration in the reactor outlet gas may be adjusted by changing the amount of the gas that is the oxygen source fed to the reactor, for example, air fed to the reactor, the reaction temperature, the pressure in the reactor, the amount of the catalyst, and the amounts of all gases fed to the reactor. By controlling the oxygen concentration in the reactor outlet gas to 3.0% by volume or less, there is a tendency that the combustion and decomposition of the produced conjugated diolefin is effectively suppressed, and the conjugated diolefin can be obtained with sufficiently good yield.

In this embodiment, the amount of carbon on the catalyst is preferably controlled to 1.0% by mass or less. In addition, even if the amount of carbon on the catalyst is more than 1.0% by mass, the desired effect in this embodiment can be continuously obtained by the operation of the reactor in this embodiment when the value of the amount of carbon can be maintained at 1.5% by mass or less. The amount of carbon on the catalyst described above can be measured by a method described in Examples described later.

(4) Purification

The reaction product obtained by the fluidized bed reaction may be purified by known techniques. For example, methods described in Japanese Patent Publication No. 45-17407, Japanese Patent Laid-Open No. 60126235, Japanese Patent Publication No. 3-48891, PETROTECH, Vol. 2, No. 4 (pp. 59 to 65, 1978), and the like may be referred to. When the conjugated diolefin concentration in the reaction product after purification is 99% or more, the reaction product can be preferably used as a high purity conjugated diolefin used for raw materials of synthetic rubbers and the like.

[2] Catalyst (1) Structure

The catalyst used in the production method in this embodiment is not particularly limited as long as it is an oxide catalyst that contains molybdenum and is brought into contact with the monoolefin having four or more carbon atoms 2 to produce the conjugated diolefin. Among the above-described catalysts, catalysts in which oxides containing molybdenum are supported on supports are preferred.

The catalyst in which an oxide is supported on a support in this embodiment preferably comprises the support and Mo, Bi, and Fe. The composition of the above Mo, Bi, and Fe is preferably adjusted to form an oxide appropriate for the purpose, and it is considered that lattice oxygen in this oxide promotes the oxidative dehydrogenation reaction of the monoolefin to the conjugated diolefin. Generally, when lattice oxygen in a catalyst is consumed in an oxidative dehydrogenation reaction, oxygen vacancies are created in the oxide. As a result, with the progress of the reaction, the reduction of the oxide proceeds, and the catalytic activity decreases. Thus, in order to maintain good catalytic activity, it is preferred that the oxide subjected to reduction is rapidly reoxidized. It is considered that in addition to reactivity for the oxidative dehydrogenation reaction of the monoolefin to the conjugated diolefin, the above oxide comprising Mo, Bi, and Fe is also excellent in reoxidation reaction in which molecular oxygen in the gas phase is absorbed and dissociated, and taken into the oxide to regenerate consumed lattice oxygen.

In this embodiment, when the catalyst in which the oxide comprising Mo, Bi, and Fe is supported on a support is used for the production of the conjugated diolefin by the fluidized bed method, there is a tendency that the secondary decomposition of the conjugated diolefin that is the product can be effectively suppressed, and the conjugated diolefin can be obtained with high yield. As a reason for this, it is considered that although the details are unclear, the acidity of the catalyst is preferred, and thus, the secondary decomposition of the conjugated diolefin on the catalyst is suppressed. As other reasons, it is considered that the adsorption capacity of the reaction active sites for the produced conjugated diolefin is small, and thus, the produced conjugated diolefin is rapidly desorbed from the catalyst before being subjected to decomposition at the reaction active sites, and the like.

In this embodiment, for the composition ratio of Mo, Bi, and Fe, the atomic ratio of Bi, p, and the atomic ratio of Fe, q, to the atomic ratio of Mo, 12, are preferably in the ranges of $0.1 \le p \le 5$ and $0.5 \le q \le 8$, from the viewpoint of easily forming an oxide appropriate for the purpose.

The oxide contained in the above oxide catalyst preferably has a composition represented by the following empirical formula:

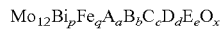

$$Mo_{12}Bi_pFe_qA_aB_bC_cD_dE_eO_x$$

(wherein A represents at least one element selected from nickel and cobalt, B represents at least one element selected from alkali metal elements, C represents at least one element selected from magnesium, calcium, strontium, barium, zinc, and manganese, D represents at least one rare earth element, E represents at least one element selected from chromium, indium, and gallium, O represents oxygen, p, q, a, b, c, d, e, and x represent the atomic ratios of bismuth, iron, A, B, C, D, E, and oxygen to 12 molybdenum atoms, respectively, $0.1 \le p \le 5$, $0.5 \le q \le 8$, $0 \le a \le 10$, $0.02 \le b \le 2$, $0 \le c \le 5$, $0 \le d \le 5$, and $0 \le e \le 5$ are satisfied, and x is the number of atoms of oxygen required to satisfy the valence requirements of the other elements present.)

An "empirical formula" represents a composition composed of the atomic ratios of metals contained in the formula, and oxygen required according to the atomic ratios and the sum of oxidation numbers herein. In an oxide comprising metals that can have various oxidation numbers, it is substantially impossible to specify the number of atoms of oxygen, and thus, the number of oxygen is formally represented by "x." For example, when a slurry comprising a Mo compound, a Bi compound, and an Fe compound is prepared, and dried and/or calcined to obtain an oxide, the atomic ratios of metals contained in the slurry, and the atomic ratios of metals in the obtained oxide may be considered substantially the same. Therefore, the empirical formula of the obtained oxide is obtained by adding $O_x$ to the set composition formula of the slurry. A formula representing intentionally controlled components and their ratio, like the set composition of the slurry described above, is referred to as a "composition formula" herein. In addition, in the case of the above-described example, the empirical formula from which $O_x$ is removed is referred to as a "composition formula."

In the above empirical formula, the roles of the arbitrary components represented by A, B, C, D, and E are not limiting, but in the field of oxide catalysts comprising Mo, Bi, and Fe as essential components, the roles are generally presumed as follows. That is, it is considered that A and E improve the activity of the catalyst, B and C stabilize the structure of the oxide comprising Mo, Bi, and Fe appropriate for the purpose, and D reoxidizes the oxide. When p, q, a, b, c, d, and e in the above empirical formula are in preferred ranges, there is a tendency that these effects increase further.

In the above empirical formula, as a more preferred composition, $0.2 \le p \le 3.0$, $0.7 \le q \le 5.0$, $1.0 \le a \le 9.0$, $0.05 \le b \le 1.0$, $1.0 \le c \le 4.0$, $0.1 \le d \le 3.0$, and $0 \le e \le 4.0$ are satisfied. As a further preferred composition, B is rubidium, potassium, or cesium, C is magnesium, D is cerium, lanthanum, praseodymium, neodymium, or yttrium, and $0.3 \le p \le 2.0$, $1.0 \le q \le 3.0$, $2.0 \le a \le 8.0$, $0.1 \le b \le 0.5$, $1.5 \le c \le 3.5$, $0.2 \le d \le 2.0$, and $0 \le e \le 3.0$ are satisfied. When the oxide has the above composition, there is a tendency that the yield of the conjugated diolefin corresponding to the monoolefin increases.

In this embodiment, the oxide is preferably supported on a support. By supporting the oxide on a support, physical properties preferred for the fluidized bed reaction, such as particle shape, size, and distribution, flowability, and mechanical strength, can be improved. The support may be effectively used in the range of preferably 30 to 70% by mass, more preferably 40 to 60% by mass, based on the total of the support and the oxide. The supported catalyst comprising the oxide containing Mo, Bi, and Fe may be produced by known methods. For example, a production method including the first step of preparing a raw material slurry, the second step of spray-drying the raw material slurry, and the third step of calcining the dry product obtained in the second step may be used. The above support is not particularly limited. One or more selected from the group consisting of silica, alumina, titania, and zirconia are preferred, and silica is particularly preferred. Silica is an inert support compared with other supports. By using silica as the support, there is a tendency that good bonding action to the catalyst can be exhibited without decreasing the activity and selectivity of the catalyst for the target product.

(2) Production Method

A preferred aspect of a method for producing a catalyst, comprising the first step of preparing a raw material slurry, the second step of spray-drying the raw material slurry, and the third step of calcining the dry product obtained in the second step will be described.

In the above first step, catalyst raw materials are mixed to prepare a raw material slurry. Examples of the sources of elements of molybdenum, bismuth, iron, nickel, cobalt, an alkali metal element, magnesium, calcium, strontium, barium, zinc, manganese, a rare earth element, chromium, indium, and gallium may include ammonium salts, nitrates, hydrochlorides, sulfates, and organic acid salts soluble in water or nitric acid. Particularly, as the molybdenum source, an ammonium salt is preferred, and as the element sources of bismuth, iron, nickel, an alkali element, magnesium, zinc, manganese, and a rare earth element, nitrates thereof are preferred. As described above, as the support for the oxide, oxides, such as silica, alumina, titania, and zirconia, can be used, but as a preferred support, silica is used. As the silica source at this time, a silica sol is preferred. Regarding impurities contained in the silica sol, preferably, a silica sol comprising 0.04 or less aluminum atoms per 100 silicon atoms is used, and more preferably, a silica sol comprising 0.02 or less aluminum atoms per 100 silicon atoms is used. The raw material slurry may be prepared, for example, by adding an ammonium salt of molybdenum dissolved in water to a silica sol, and then adding a solution in which nitrates of elements of bismuth, a rare earth element, iron, nickel, magnesium, zinc, manganese, and an alkali element are dissolved in water or an aqueous nitric acid solution. At this time, the above sequence of addition may also be changed.

In the above second step, the raw material slurry obtained in the above first step is spray-dried to obtain spherical particles. The atomization of the raw material slurry may be usually performed by methods, such as a centrifugal method, a two-fluid nozzle method, and a high pressure nozzle method, which are industrially carried out, and is particularly preferably performed by the centrifugal method. Next, the obtained particles are dried. As the drying heat source, steam, or air heated by an electrical heater or the like is preferably used. The temperature of the dryer inlet may be 100 to 400° C., preferably 150 to 300° C.

In the above third step, the dry particles obtained in the second step are calcined to obtain the desired catalyst. For the calcining of the dry particles, it is preferred that precalcining is performed at 150 to 500° C. if necessary, and then, calcining is performed in the temperature range of 500 to 700° C. for 1 to 20 hours. The calcining step may be performed using a calcining furnace, such as a rotary furnace, a tunnel furnace, or a muffle furnace.

The average particle diameter of the obtained catalyst is preferably in the range of 40 to 70 μm, more preferably 50 to 60 μm, and it is preferred that 90% by mass or more of the catalyst particles are distributed in the range of 10 to 150 μm. Here, the average particle diameter of the catalyst can be measured using a laser diffraction/three-stage particle size distribution measuring apparatus LA-300 manufactured by HORIBA, Ltd.

EXAMPLES

The present invention will be described in more detail below by giving Examples, but the present invention is not limited by the Examples described below.

In Examples and Comparative Examples, the monoolefin conversion rate, and conjugated diene selectivity and yield used to represent reaction results are defined by the following formulas.

monoolefin conversion rate (%)=(the number of moles of the reacted monoolefin)/(the number of moles of the fed monoolefin)*100 conjugated diene selectivity (%)=(the number of moles of the produced conjugated diene)/(the number of moles of the reacted monoolefin)*100 conjugated diene yield (%)=(the number of moles of the produced conjugated diene)/(the number of moles of the fed monoolefin)*100

The amount of carbon contained on the catalyst was measured at 900° C. by using MICRO CORDER JM10 manufactured by J-SCIENCE LAB Co., Ltd., and a sample in an amount of 80 to 90 mg, and feeding helium at 200 mL/min and oxygen at 15 mL/min.

As the fluidized bed reactor, a reactor made of carbon steel having an inner diameter of 0.6 m and a height of 17 m was used. It should be noted that the internal configuration of the above reactor had a two-stage cyclone, and a plurality of cooling tubes installed substantially equally divided into 4 stages with respect to the height direction. An oxygen-containing gas comprising oxygen and an inert gas, such as nitrogen, was fed from the reactor bottom using 7 nozzles, and a monoolefin that was a raw material was fed with the distance from the reactor bottom and the number changed. The above 7 nozzles were one nozzle disposed in the central portion at the reactor bottom, and 6 nozzles disposed at intervals of 60° at a distance of 200 mm from the central portion, 7 nozzles in total. The temperature of the catalyst layer was the average value of measured values by 4 thermocouples installed at positions 0.25 m to 0.5 m from the fluidized bed bottom, and the dilute layer temperature was a measured value of a thermocouple installed at the same height as the cyclone inlet located at 16.0 m from the fluidized bed bottom.

The contact time is defined by the following formula.

contact time (sec·g/cc)=$W/F*273.15/(273.15+T)*(P*1000+101.325)/101.325$ (wherein W represents the amount of the catalyst packed (g), F represents the flow rates of all feed gases (cc/sec, in terms of NTP), T represents reaction temperature (° C.), and P represents reaction pressure (MPa).)

The reaction gases were analyzed using gas chromatography (TCD and FID).

Example 1

(a) Preparation of Catalyst

A catalyst in which a metal oxide represented by the empirical formula $Mo_{12}Bi_{0.60}Fe_{1.8}Ni_{5.0}K_{0.09}Rb_{0.05}Mg_{2.0}Ce_{0.75}O_x$ was supported on 50% by mass of silica based on the entire catalyst was prepared as follows.

5.9 kg of bismuth nitrate [$Bi(NO_3)_3 \cdot 5H_2O$], 6.6 kg of cerium nitrate [$Ce(NO_3)_3 \cdot 6H_2O$], 14.7 kg of iron nitrate [$Fe(NO_3)_3 \cdot 9H_2O$], 29.3 kg of nickel nitrate [$Ni(NO_3)_2 \cdot 6H_2O$], 10.4 kg of magnesium nitrate [$Mg(NO_3)_2 \cdot 6H_2O$], 0.18 kg of potassium nitrate [$KNO_3$], and 0.15 kg of rubidium nitrate [$RbNO_3$] were dissolved in 41.3 kg of 16.6% by mass nitric acid. The solution was added to 183.5 kg of a silica sol comprising 30% by mass of $SiO_2$, and finally, a liquid in which 42.7 kg of ammonium paramolybdate [$(NH_4)_6Mo_7O_{24} \cdot 4H_2O$] was dissolved in 86.1 kg of water was added. The obtained raw material-blended liquid was fed to a co-current spray dryer, and dried at an inlet temperature of about 250° C. and an outlet temperature of about 140° C. The atomization of the above blended liquid was performed using a atomization apparatus comprising a dish-shaped rotor installed at the center of the upper portion of the dryer. The obtained powder was subjected to precalcining in an electric rotary furnace under an air atmosphere at about 350° C. for 1 hour. The powder after the precalcining was subjected to main calcining under an air atmosphere at 590° C. for 2 hours to obtain a catalyst. This catalyst preparation was repeated to produce the required amount of the catalyst. The average particle diameter of the produced catalyst was 50.5 μm. It should be noted that the average particle diameter of the catalyst was measured by a laser diffraction/three-stage particle size distribution measuring apparatus LA-300 manufactured by HORIBA, Ltd.

(b) 1,3-Butadiene Production Reaction 550 kg of the obtained catalyst was packed in the above reactor, and an oxygen-containing gas (a mixed gas of air and nitrogen) was fed from the oxygen-containing gas feed nozzles at the reactor bottom. In addition, 1-butene was fed at the same ratio from seven feed nozzles installed downward at positions 350 mm above the oxygen-containing gas feed nozzles and opposed to the oxygen-containing gas feed nozzles on a 1:1 basis. The nozzle density was 24.8 nozzles/m². A reaction was performed under the conditions of the composition (molar ratio) of the fed gases: 1-butene/air/nitrogen=1/5.4/balance, 1-butene concentration: 8% by volume, contact time: 3.0 (g·sec/cc), the temperature of the catalyst layer: 360° C., dilute layer temperature: 350° C., and reaction pressure: 0.05 MPa/G. The conversion rate of 1-butene after 10 hours from the start of the reaction was 99.0%, the selectivity of butadiene was 87.5%, the butadiene yield was 86.6%, the oxygen concentration in the outlet gas was 0.5% by volume, and the amount of carbon on the catalyst was 0% by mass. It should be noted that the above "balance" was the molar ratio of nitrogen required to set the 1-butene concentration to 8% by volume. The operation was continued under these conditions for 20 days. The conversion rate of 1-butene was 99.1%, the selectivity of butadiene was 87.4%, the butadiene yield was 86.6%, the oxygen concentration in the outlet gas was 0.5% by volume, and the amount of carbon on the catalyst was 0.6% by mass. Further, 10 days of operation was continued, and as a result, the conversion rate of 1-butene was 99.0%, the selectivity of butadiene was 87.4%, the butadiene yield was 86.5%, the oxygen concentration in the outlet gas was 0.5% by volume, and the amount of carbon on the catalyst was 0.6% by mass. Thus, the operation was stably continued.

Example 2

A reaction was performed under the same conditions as Example 1 except that 1-butene was fed at positions 700 mm above the oxygen-containing gas feed nozzles, the amount of the catalyst was 650 kg, and the contact time was 3.5 (g·sec/cc). The conversion rate of 1-butene after 10 hours from the start of the reaction was 98.5%, the selectivity of butadiene was 85.8%, the butadiene yield was 84.5%, the oxygen concentration in the outlet gas was 0.4% by volume, and the amount of carbon on the catalyst was 0% by mass. The operation was continued under these conditions for 20 days. The conversion rate of 1-butene was 98.4%, the selectivity of butadiene was 85.7%, the butadiene yield was 84.3%, the oxygen concentration in the outlet gas was 0.4% by volume, and the amount of carbon on the catalyst was 0.3% by mass. Further, 10 days of operation was continued, and as a result, the conversion rate of 1-butene was 98.3%, the selectivity of butadiene was 85.6%, the butadiene yield was 84.1%, the oxygen concentration in the outlet gas was 0.5% by volume, and the amount of carbon on the catalyst was 0.3% by mass. Thus, the operation was stably continued.

Comparative Example 1

A reaction was performed under the same conditions as Example 2, except that 40% by volume of an oxygen-containing gas composed of oxygen and nitrogen was fed from the bottom of the reactor, and the remaining 60% by volume of the oxygen-containing gas was fed upward opposed to the 1-butene feed nozzles from positions 150 mm below. The conversion rate of 1-butene after 10 hours from the start of the reaction was 98.7%, the selectivity of butadiene was 86.0%, the butadiene yield was 84.9%, the oxygen concentration in the outlet gas was 0.3% by volume, and the amount of carbon on the catalyst was 0% by mass. The operation was continued under these conditions for 20 days. The conversion rate of 1-butene was 98.4%, the selectivity of butadiene was 85.8%, the butadiene yield was 84.4%, the oxygen concentration in the outlet gas was 0.3% by volume, and the amount of carbon on the catalyst increased to 1.0% by mass. Further, the operation was continued with the composition (molar ratio) of gases changed to 1-butene/air/nitrogen=1/5.6/balance. After 5 days, the conversion rate of 1-butene was 98.8%, the selectivity of butadiene was 84.8%, the butadiene yield was 83.8%, the oxygen concentration in the outlet gas was 0.3% by volume, and the amount of carbon on the catalyst increased to 2.2% by mass. Therefore, it was determined that stable operation was difficult, and the reaction was stopped.

Example 3

A reaction was performed under the same conditions as Example 2 except that 1-butene was fed at positions 350 mm and 700 mm above the oxygen-containing gas feed nozzles, each at a ratio of 1/2. The weighted mean value of the 1-butene feed positions was 525 mm. The conversion rate of 1-butene after 10 hours from the start of the reaction was 98.0%, the selectivity of butadiene was 85.3%, the butadiene yield was 83.6%, the oxygen concentration in the outlet gas was 0.4% by volume, and the amount of carbon on the catalyst was 0% by mass. The operation was continued under these conditions for 20 days. The conversion rate of 1-butene was 98.0%, the selectivity of butadiene was 85.3%, the butadiene yield was 83.6%, the oxygen concentration in the outlet gas was 0.4% by volume, and the amount of carbon on the catalyst was 0.2% by mass. Further, 10 days of operation was continued, and as a result, the conversion rate of 1-butene was 97.9%, the selectivity of butadiene was 85.2%, the butadiene yield was 83.4%, the oxygen concentration in the outlet gas was 0.4% by volume, and the amount of carbon on the catalyst was 0.2% by mass. Thus, the operation was stably continued.

Example 4

A reaction was performed under the same conditions as Example 1 except that 1-butene was fed at positions 1500 mm above the oxygen-containing gas feed nozzles, the amount of the catalyst was 750 kg, the composition (molar ratio) of fed gases was 1-butene/air/nitrogen=1/5.7/balance, the number of feed nozzles for butene was 9, and the contact time was 4.1 (g·sec/cc). It should be noted that, for the above 9 nozzles, one nozzle was disposed in the central portion. Further, the remaining 8 nozzles were disposed at such eight points that were at positions 200 mm from the above center and at intervals of 45°. The nozzle density was 31.8 nozzles/m$^2$. The conversion rate of 1-butene after 10 hours from the start of the reaction was 98.5%, the selectivity of butadiene was 86.5%, the butadiene yield was 85.2%, the oxygen concentration in the outlet gas was 0.7% by volume, and the amount of carbon on the catalyst was 0% by mass. The operation was continued under these conditions for 20 days. The conversion rate of 1-butene was 98.5%, the selectivity of butadiene was 86.4%, the butadiene yield was 85.1%, the oxygen concentration in the outlet gas was 0.7% by volume, and the amount of carbon on the catalyst was 0.1% by mass. Further, 10 days of operation was continued, and as a result, the conversion rate of 1-butene was 98.4%, the selectivity of butadiene was 86.3%, the butadiene yield was 84.9%, the oxygen concentration in the outlet gas was 0.7% by volume, and the amount of carbon on the catalyst was 0.1% by mass. Thus, the operation was stably continued.

Comparative Example 2

A reaction was performed under the same conditions as Example 1, except that 1-butene was fed at positions 75 mm above the oxygen-containing gas feed nozzles. The conversion rate of 1-butene after 10 hours from the start of the reaction was 99.3%, the selectivity of butadiene was 88.0%, the butadiene yield was 87.3%, the oxygen concentration in the outlet gas was 0.4% by volume, and the amount of carbon on the catalyst was 0% by mass. The operation was continued under these conditions for 20 days. The conversion rate of 1-butene was 98.9%, the selectivity of butadiene was 87.3%, the butadiene yield was 86.3%, the oxygen concentration in the outlet gas was 0.4% by volume, and the amount of carbon on the catalyst increased to 2.1% by mass. Further, the operation was continued with the composition (molar ratio) of gases changed to 1-butene/air/nitrogen=1/5.6/balance. After 3 days, the conversion rate of 1-butene was 99.2%, the selectivity of butadiene was 86.3%, the butadiene yield was 85.6%, the oxygen concentration in the outlet gas was 0.4% by volume, and the amount of carbon on the catalyst increased to 3.2% by mass. Therefore, it was determined that stable operation was difficult, and the reaction was stopped.

Example 5

A reaction was performed under the same conditions as Example 1, except that the number of feed nozzles for 1-butene was 13. It should be noted that, for the above 13 nozzles, one nozzle was disposed in the central portion. In addition, 6 nozzles of the remaining 12 nozzles were disposed at such six points that were at positions 150 mm and 0° from the above center and at intervals of 60°. Further, the remaining 6 nozzles were disposed at such six points that were at positions 200 mm and 30° from the above center and at intervals of 60°. The nozzle density was 46.0 nozzles/m$^2$. The conversion rate of 1-butene after 10 hours from the start of the reaction was 99.0%, the selectivity of butadiene was 87.1%, the butadiene yield was 86.2%, the oxygen concentration in the outlet gas was 0.5% by volume, and the amount of carbon on the catalyst was 0% by mass. The operation was continued under these conditions for 20 days. The conversion rate of 1-butene was 99.0%, the selectivity of butadiene was 87.0%, the butadiene yield was 86.1%, the oxygen concentration in the outlet gas was 0.5% by volume, and the amount of carbon on the catalyst was 0.5% by mass. Further, 10 days of operation was continued, and as a result, the conversion rate of 1-butene was 98.9%, the selectivity of butadiene was 86.9%, the butadiene yield was 85.9%, the oxygen concentration in the outlet gas was 0.5% by volume, and the amount of carbon on the catalyst was 0.5% by mass. Thus, the operation was stably continued.

Example 6

A reaction was performed under the same conditions as Example 1, except that the number of feed nozzles for 1-butene and the number of feed nozzles for the oxygen-containing gas was 4. The above 4 nozzles were disposed at such four points that were at positions 175 mm from the center and at intervals of 90°. The nozzle density was 14.2 nozzles/m$^2$. The conversion rate of 1-butene after 10 hours from the start of the reaction was 98.8%, the selectivity of butadiene was 87.1%, the butadiene yield was 86.1%, the oxygen concentration in the outlet gas was 0.5% by volume, and the amount of carbon on the catalyst was 0% by mass. The operation was continued under these conditions for 20 days. The conversion rate of 1-butene was 98.7%, the selectivity of butadiene was 87.0%, the butadiene yield was 85.9%, the oxygen concentration in the outlet gas was 0.5% by volume, and the amount of carbon on the catalyst was 0.5% by mass. Further, 10 days of operation was continued, and as a result, the conversion rate of 1-butene was 98.7%, the selectivity of butadiene was 87.0%, the butadiene yield was 85.9%, the oxygen concentration in the outlet gas was 0.5% by volume, and the amount of carbon on the catalyst was 0.5% by mass. Thus, the operation was stably continued.

Example 7

A reaction was performed under the same conditions as Example 1, except that the number of feed nozzles for 1-butene and the number of feed nozzles for the oxygen-containing gas was 3. The above 3 nozzles were disposed at such three points that were at positions 175 mm from the center and at intervals of 120°. The nozzle density was 10.6 nozzles/m$^2$. The conversion rate of 1-butene after 10 hours from the start of the reaction was 98.0%, the selectivity of butadiene was 86.5%, the butadiene yield was 84.8%, the oxygen concentration in the outlet gas was 0.7% by volume, and the amount of carbon on the catalyst was 0% by mass. The operation was continued under these conditions for 20 days. The conversion rate of 1-butene was 97.8%, the selectivity of butadiene was 86.5%, the butadiene yield was 84.6%, the oxygen concentration in the outlet gas was 0.7% by volume, and the amount of carbon on the catalyst was 0.5% by mass. Further, 10 days of operation was continued, and as a result, the conversion rate of 1-butene was 97.7%, the selectivity of butadiene was 86.3%, the butadiene yield was 84.3%, the oxygen concentration in the outlet gas was 0.7% by volume, and the amount of carbon on the catalyst was 0.5% by mass. Thus, the operation was stably continued.

Example 8

A reaction was performed under the same conditions as Example 1, except that in Example 1, 1-butene was fed at positions 100 mm above the oxygen-containing gas feed nozzles, the composition (molar ratio) of fed gases was 1-butene/air/water/nitrogen=1/5.4/2/balance, and the 1-butene concentration was 6% by volume. It should be noted that the water was fed entrained in the oxygen-containing gas. The conversion rate of 1-butene after 10 hours from the start of the reaction was 99.2%, the selectivity of butadiene was 88.2%, the butadiene yield was 87.5%, the oxygen concentration in the outlet gas was 0.5% by volume, and the amount of carbon on the catalyst was 0% by mass. The operation was continued under these conditions for 20 days. The conversion rate of 1-butene was 99.2%, the selectivity of butadiene was 88.1%, the butadiene yield was 87.4%, the oxygen concentration in the outlet gas was 0.5% by volume, and the amount of carbon on the catalyst was 0.2% by mass. Further, 10 days of operation was continued, and as a result, the conversion rate of 1-butene was 99.1%, the selectivity of butadiene was 88.0%, the butadiene yield was 87.2%, the oxygen concentration in the outlet gas was 0.5% by volume, and the amount of carbon on the catalyst was 0.2% by mass. Thus, the operation was stably continued.

Example 9

A reaction was performed under the same conditions as Example 2, except that the amount of the catalyst was 700 kg, the contact time was 3.9 (sec·g/cc), the composition (molar ratio) of fed gases was 1-butene/air/water/nitrogen=1/5.8/2/balance, and the 1-butene concentration was 10% by volume. It should be noted that the water was fed entrained in the oxygen-containing gas. The conversion rate of 1-butene after 10 hours from the start of the reaction was 98.4%, the selectivity of butadiene was 84.4%, the butadiene yield was 83.0%, the oxygen concentration in the outlet gas was 0.5% by volume, and the amount of carbon on the catalyst was 0% by mass. The operation was continued under these conditions for 20 days. The conversion rate of 1-butene was 98.2%, the selectivity of butadiene was 84.3%, the butadiene yield was 82.8%, the oxygen concentration in the outlet gas was 0.5% by volume, and the amount of carbon on the catalyst was 0.5% by mass. Further, 10 days of operation was continued, and as a result, the conversion rate of 1-butene was 98.0%, the selectivity of butadiene was 84.3%, the butadiene yield was 82.6%, the oxygen concentration in the outlet gas was 0.5% by volume, and the amount of carbon on the catalyst was 0.5% by mass. Thus, the operation was stably continued.

Example 10

A reaction was performed under the same conditions as Example 2, except that the amount of the catalyst was 700 kg, the contact time was 4.1 (sec·g/cc), a raffinate-2 comprising 42% by weight of 1-butene, 30% by weight of 2-butene, 1% by weight of isobutene, 20% by weight of n-butane, and 5% by weight of isobutane was fed instead of 1-butene, the composition (molar ratio) of gases was n-butene (1-butene and 2-butene)/air/nitrogen=1/5.4/balance, and the concentration of n-butene was 8% by volume. The conversion rate of n-butene after 10 hours from the start of the reaction was 92.1%, the selectivity of butadiene was 82.2%, the butadiene yield was 75.7%, the oxygen concentration in the outlet gas was 0.5% by volume, and the amount of carbon on the catalyst was 0% by mass. The operation was continued under these conditions for 20 days. The conversion rate of n-butene was 92.0%, the selectivity of butadiene was 82.1%, the butadiene yield was 75.5%, the oxygen concentration in the outlet gas was 0.5% by volume, and the amount of carbon on the catalyst was 0.2% by mass. Further, 10 days of operation was continued, and as a result, the conversion rate of n-butene was 91.9%, the selectivity of butadiene was 82.0%, the butadiene yield was 75.4%, the oxygen concentration in the outlet gas was 0.5% by volume, and the amount of carbon on the catalyst was 0.2% by mass. Thus, the operation was stably continued.

Example 11

A reaction was performed under the same conditions as Example 1, except that a catalyst in which a metal oxide whose composition was represented by $Mo_{12}Bi_{0.45}Fe_{1.8}Ni_{2.5}Co_{4.5}Rb_{0.12}Ce_{0.90}O_x$ was supported on 40% by weight of silica based on the entire catalyst was calcined at 550° C. The conversion rate of 1-butene after 10 hours from the start of the reaction was 98.5%, the selectivity of butadiene was 88.5%, the butadiene yield was 87.2%, the oxygen concentration in the outlet gas was 0.5% by volume, and the amount of carbon on the catalyst was 0% by mass. The operation was continued under these conditions for 20 days. The conversion rate of 1-butene was 98.5%, the selectivity of butadiene was 88.4%, the butadiene yield was 87.1%, the oxygen concentration in the outlet gas was 0.5% by volume, and the amount of carbon on the catalyst was 0.4% by mass. Further, 10 days of operation was continued, and as a result, the conversion rate of 1-butene was 98.4%, the selectivity of butadiene was 88.3%, the butadiene yield was 86.9%, the oxygen concentration in the outlet gas was 0.5% by volume, and the amount of carbon on the catalyst was 0.4% by mass. Thus, the operation was stably continued.

Example 12

A reaction was performed under the same conditions as Example 1, except that the 1-butene feed nozzles were installed upward. The conversion rate of 1-butene after 10 hours from the start of the reaction was 97.0%, the selectivity of butadiene was 86.5%, the butadiene yield was 83.9%, the oxygen concentration in the outlet gas was 0.6% by volume, and the amount of carbon on the catalyst was 0% by mass. The operation was continued under these conditions for 20 days. The conversion rate of 1-butene was 96.8%, the selectivity of butadiene was 86.6%, the butadiene yield was 83.8%, the oxygen concentration in the outlet gas was 0.6% by volume, and the amount of carbon on the catalyst was 0.5% by mass. Further, 10 days of operation was continued, and as a result, the conversion rate of 1-butene was 96.7%, the selectivity of butadiene was 86.5%, the butadiene yield was 83.6%, the oxygen concentration in the outlet gas was 0.6% by volume, and the amount of carbon on the catalyst was 0.5% by mass. Thus, the operation was stably continued.

Example 13

A reaction was performed under the same conditions as Example 2, except that 70% by volume of an oxygen-containing gas composed of oxygen and nitrogen was fed from the bottom of the reactor, and the remaining 30% by volume of the oxygen-containing gas was fed upward opposed to the 1-butene feed nozzles from positions 150 mm below. The conversion rate of 1-butene after 10 hours from the start of the reaction was 98.8%, the selectivity of butadiene was 86.1%, the butadiene yield was 85.1%, the oxygen concentration in the outlet gas was 0.3% by volume, and the amount of carbon on the catalyst was 0% by mass. The operation was continued under these conditions for 20 days. The conversion rate of 1-butene was 98.7%, the selectivity of butadiene was 86.0%, the butadiene yield was 84.9%, the oxygen concentration in the outlet gas was 0.4% by volume, and the amount of carbon on the catalyst was 0.5% by mass. Further, 10 days of operation was continued, and as a result, the conversion rate of 1-butene was 98.7%, the selectivity of butadiene was 85.9%, the butadiene yield was 84.8%, the oxygen concentration in the outlet gas was 0.4% by volume, and the amount of carbon on the catalyst was 0.5% by mass. Thus, the operation was stably continued.

Example 14

A reaction was performed under the same conditions as Example 2, except that a gas obtained by mixing 1-butene with the same amount of nitrogen was fed to the reactor. The conversion rate of 1-butene after 10 hours from the start of the reaction was 98.7%, the selectivity of butadiene was 86.0%, the butadiene yield was 84.9%, the oxygen concentration in the outlet gas was 0.3% by volume, and the amount of carbon on the catalyst was 0% by mass. The operation was continued under these conditions for 20 days. The conversion rate of 1-butene was 98.8%, the selectivity of butadiene was 86.0%, the butadiene yield was 85.0%, the oxygen concentration in the outlet gas was 0.3% by volume, and the amount of carbon on the catalyst was 0.2% by mass.

Further, 10 days of operation was continued, and as a result, the conversion rate of 1-butene was 98.7%, the selectivity of butadiene was 86.0%, the butadiene yield was 84.9%, the oxygen concentration in the outlet gas was 0.3% by volume, and the amount of carbon on the catalyst was 0.2% by mass. Thus, the operation was stably continued.

Example 15

A reaction was performed under the same conditions as Example 2, except that a network structure that was a wire net (made of SUS304) having a diameter of 3 mm and had an opening (b, b') of 30 mm was installed at positions 1000 mm and 1500 mm above the oxygen-containing gas feed nozzles. It should be noted that the opening ratio of the above network structure was 83%. The conversion rate of 1-butene after 10 hours from the start of the reaction was 98.9%, the selectivity of butadiene was 86.0%, the butadiene yield was 85.1%, the oxygen concentration in the outlet gas was 0.4% by volume, and the amount of carbon on the catalyst was 0% by mass. The operation was continued under these conditions for 20 days. The conversion rate of 1-butene was 98.8%, the selectivity of butadiene was 85.9%, the butadiene yield was 84.9%, the oxygen concentration in the outlet gas was 0.4% by volume, and the amount of carbon on the catalyst was 0.4% by mass. Further, 10 days of operation was continued, and as a result, the conversion rate of 1-butene was 98.7%, the selectivity of butadiene was 85.8%, the butadiene yield was 84.7%, the oxygen concentration in the outlet gas was 0.4% by volume, and the amount of carbon on the catalyst was 0.4% by mass. Thus, the operation was stably continued.

Example 16

A reaction was performed under the same conditions as Example 15, except that a network structure that was a wire net having a diameter of 3 mm and had an opening (b, b') of 70 mm was used. It should be noted that the opening ratio of the above network structure was 92%. The conversion rate of 1-butene after 10 hours from the start of the reaction was 98.7%, the selectivity of butadiene was 86.0%, the butadiene yield was 84.8%, the oxygen concentration in the outlet gas was 0.4% by volume, and the amount of carbon on the catalyst was 0% by mass. The operation was continued under these conditions for 20 days. The conversion rate of 1-butene was 98.6%, the selectivity of butadiene was 86.0%, the butadiene yield was 84.8%, the oxygen concentration in the outlet gas was 0.4% by volume, and the amount of carbon on the catalyst was 0.3% by mass. Further, 10 days of operation was continued, and as a result, the conversion rate of 1-butene was 98.5%, the selectivity of butadiene was 86.0%, the butadiene yield was 84.7%, the oxygen concentration in the outlet gas was 0.4% by volume, and the amount of carbon on the catalyst was 0.3% by mass. Thus, the operation was stably continued.

Example 17

A reaction was performed under the same conditions as Example 2 except that the amount of the catalyst was 350 kg, the temperature of the catalyst layer was 365° C., the dilute layer temperature was 355° C., and the composition (molar ratio) of fed gases was 1-butene:air:nitrogen=1/4.8/balance. At this time, the contact time was 1.9 (g·sec/cc). The conversion rate of 1-butene after 10 hours from the start of the reaction was 99.0%, the selectivity of butadiene was 88.8%, the butadiene yield was 87.9%, the oxygen concentration in the outlet gas was 0.4% by volume, and the amount of carbon on the catalyst was 0% by mass. The operation was continued under these conditions for 20 days. The conversion rate of 1-butene was 98.9%, the selectivity of butadiene was 88.7%, the butadiene yield was 87.7%, the oxygen concentration in the outlet gas was 0.4% by volume, and the amount of carbon on the catalyst was 0.2% by mass. Further, 10 days of operation was continued, and as a result, the conversion rate of 1-butene was 98.8%, the selectivity of butadiene was 88.7%, the butadiene yield was 87.6%, the oxygen concentration in the outlet gas was 0.4% by volume, and the amount of carbon on the catalyst was 0.2% by mass. Thus, the operation was stably continued.

Example 18

A reaction was performed under the same conditions in Example 1, except that the number of feed nozzles for 1-butene and the number of feed nozzles for the oxygen-containing gas was 2. The above 2 nozzles were disposed at such two points that were at positions 175 mm from the center and at intervals of 180°. The nozzle density was 7.1 nozzles/m$^2$. The conversion rate of 1-butene after 10 hours from the start of the reaction was 95.3%, the selectivity of butadiene was 84.0%, the butadiene yield was 80.1%, the oxygen concentration in the outlet gas was 0.7% by volume, and the amount of carbon on the catalyst was 0% by mass. The operation was continued under these conditions for 20 days. The conversion rate of 1-butene was 95.2%, the selectivity of butadiene was 84.0%, the butadiene yield was 80.0%, the oxygen concentration in the outlet gas was 0.7% by volume, and the amount of carbon on the catalyst was 0.2% by mass.

Example 19

A reaction was performed under the same conditions as Example 2 except that 1-butene was fed at positions 1400 mm above the oxygen-containing gas feed nozzles, the amount of the catalyst was 700 kg, the contact time was 3.9 (sec·g/cc), the temperature of the catalyst layer was 365° C., the dilute layer temperature was 360° C., the composition (molar ratio) of fed gases was 1-butene:air=1/5.8, and the 1-butene concentration was 14.7% by volume. The conversion rate of 1-butene after 10 hours from the start of the reaction was 97.0%, the selectivity of butadiene was 81.5%, the butadiene yield was 77.5%, the oxygen concentration in the outlet gas was 1.5% by volume, and the amount of carbon on the catalyst was 0% by mass. The operation was continued under these conditions for 20 days. The conversion rate of 1-butene was 96.8%, the selectivity of butadiene was 81.3%, the butadiene yield was 78.7%, the oxygen concentration in the outlet gas was 1.5% by volume, and the amount of carbon on the catalyst was 0.7% by mass. Further, 10 days of operation was continued, and as a result, the conversion rate of 1-butene was 96.7%, the selectivity of butadiene was 81.2%, the butadiene yield was 78.5%, the oxygen concentration in the outlet gas was 1.5% by volume, and the amount of carbon on the catalyst was 0.7% by mass. Thus, the operation was stably continued.

This application is based on Japanese Patent Application No. 2012-230223 filed on Oct. 17, 2012, the content of which is incorporated herein by reference.

INDUSTRIAL APPLICABILITY

According to the present invention, carbon adhering to a catalyst can be suppressed, and from a monoolefin having four or more carbon atoms, the corresponding conjugated diolefin can be stably produced.

REFERENCE SIGNS LIST 1A, 1B, 1B', 1C, 1D: a fluidized bed reactor
2: a monoolefin having four or more carbon atoms
3: an oxygen-containing gas
4: a reaction-produced gas
5: a network structure
6: an oxide catalyst containing molybdenum

The invention claimed is:

1. A method for producing a conjugated diolefin, the method comprising:
feeding a monoolefin having four or more carbon atoms and an oxygen-containing gas into a fluidized bed reactor having an oxide catalyst containing molybdenum therein, and bringing the oxide catalyst, the monoolefin having four or more carbon atoms, and the oxygen-containing gas into contact with each other to produce a conjugated diolefin,
wherein at least 50% or more of a total amount of the oxygen-containing gas is fed from an oxygen-containing gas feed nozzle located at a bottom of the fluidized bed reactor,
wherein the monoolefin having four or more carbon atoms is fed from a plurality of monoolefin feed nozzles installed at n places located at heights a1, a2, . . . , and an from the oxygen-containing gas feed nozzle, respectively,
wherein the plurality of monoolefin feed nozzles at the heights a1, a2, . . . , and an feed the monoolefin having four or more carbon atoms at ratios of b1, b2, . . . , and bn, respectively, based on a total amount of the monoolefin having four or more carbon fed into the fluidized bed reactor such that b1+b2+ . . . +bn=1, and
wherein a weighted mean value represented by the following formula is 100 mm or greater:

weighted mean value=$a1*b1+a2*b2+ \ldots +an*bn$.

2. The method for producing a conjugated diolefin according to claim 1, wherein a number of the plurality of monoolefin feed nozzles per unit is $10/m^2$ or more.

3. The method for producing a conjugated diolefin according to claim 1, wherein a network structure having an opening ratio of 60% or more is disposed above at least one of the plurality of monoolefin feed nozzles.

4. The method for producing a conjugated diolefin according to claim 3, wherein the weighted mean value ranges from 100 mm to 3000 mm.

5. The method for producing a conjugated diolefin according to claim 4, wherein the monoolefin having four or more carbon atoms is n-butene or isopentene.

6. The method for producing a conjugated diolefin according to claim 5, wherein the oxide is represented by the following empirical formula, and the support is one or more selected from the group consisting of silica, alumina, titania, and zirconia, $$Mo_{12}Bi_pFe_qA_aB_bC_cD_dE_eO_x$$

wherein A is at least one element selected from nickel and cobalt, B is at least one element selected from alkali metal elements, C is at least one element selected from magnesium, calcium, strontium, barium, zinc, and manganese, D is at least one rare earth element, E is at least one element selected from chromium, indium, and gallium, O is oxygen, p, q, a, b, c, d, e, and x represent atomic ratios of bismuth, iron, A, B, C, D, E, and oxygen to 12 molybdenum atoms, respectively, $0.1 \leq p \leq 5$, $0.5 \leq q \leq 8$, $0 \leq a \leq 10$, $0.02 \leq b \leq 2$, $0 \leq c \leq 5$, $0 \leq d \leq 5$, and $0 \leq e \leq 5$ are satisfied, and x is a number of atoms of oxygen required to satisfy valence requirements of other elements present.

7. The method for producing a conjugated diolefin according to claim 6, wherein the monoolefin having four or more carbon atoms, and at least one gas selected from the group consisting of nitrogen, water vapor, and carbon dioxide are fed from the plurality of monoolefin feed nozzles.

8. The method for producing a conjugated diolefin according to claim 1, wherein the weighted mean value ranges from 100 mm to 3000 mm.

9. The method for producing a conjugated diolefin according to claim 8, wherein the monoolefin having four or more carbon atoms is n-butene or isopentene.

10. The method for producing a conjugated diolefin according to claim 9, wherein the oxide is represented by the following empirical formula, and the support is one or more selected from the group consisting of silica, alumina, titania, and zirconia, $$Mo_{12}Bi_pFe_qA_aB_bC_cD_dE_eO_x$$

wherein A is at least one element selected from nickel and cobalt, B is at least one element selected from alkali metal elements, C is at least one element selected from magnesium, calcium, strontium, barium, zinc, and manganese, D is at least one rare earth element, E is at least one element selected from chromium, indium, and gallium, O is oxygen, p, q, a, b, c, d, e, and x represent atomic ratios of bismuth, iron, A, B, C, D, E, and oxygen to 12 molybdenum atoms, respectively, $0.1 \leq p \leq 5$, $0.5 \leq q \leq 8$, $0 \leq a \leq 10$, $0.02 \leq b \leq 2$, $0 \leq c \leq 5$, $0 \leq d \leq 5$, and $0 \leq e \leq 5$ are satisfied, and x is a number of atoms of oxygen required to satisfy valence requirements of other elements present.

11. The method for producing a conjugated diolefin according to claim 10, wherein the monoolefin having four or more carbon atoms, and at least one gas selected from the group consisting of nitrogen, water vapor, and carbon dioxide are fed from the plurality of monoolefin feed nozzles.

12. The method for producing a conjugated diolefin according to claim 1, wherein an oxygen concentration of a reactor outlet gas ranges from 0.2% by volume to 2.0% by volume.

13. The method for producing a conjugated diolefin according to claim 1, wherein the weighted mean value is 200 mm or greater.

* * * * *